(12) United States Patent
Paik et al.

(10) Patent No.: US 10,656,154 B2
(45) Date of Patent: May 19, 2020

(54) METHODS FOR DETECTING AN AMOUNT OF COMPLEMENT FACTOR B PROTEIN AND CARBOHYDRATE ANTIGEN 19-9 PROTEIN, AND METHODS FOR DIAGNOSING AND TREATING PANCREATIC CANCER USING THE SAME

(71) Applicant: JW HOLDINGS CORPORATION, Seoul (KR)

(72) Inventors: Young Ki Paik, Seoul (KR); Min Jung Lee, Gyeonggi-do (KR)

(73) Assignee: JW HOLDINGS CORPORATION, Seoul (KR)

( * ) Notice: Subject to any disclaimer, the term of this patent is extended or adjusted under 35 U.S.C. 154(b) by 0 days.

(21) Appl. No.: 15/347,812

(22) Filed: Nov. 10, 2016

(65) Prior Publication Data
US 2017/0153239 A1 Jun. 1, 2017

Related U.S. Application Data

(63) Continuation-in-part of application No. PCT/KR2014/008242, filed on Sep. 3, 2014.

(30) Foreign Application Priority Data

May 12, 2014 (KR) .................. 10-2014-0056585

(51) Int. Cl.
*G01N 33/574* (2006.01)
*G01N 30/72* (2006.01)
*G01N 23/00* (2006.01)
*G01N 33/561* (2006.01)
*G01N 27/26* (2006.01)

(52) U.S. Cl.
CPC ....... *G01N 33/57438* (2013.01); *G01N 23/00* (2013.01); *G01N 27/26* (2013.01); *G01N 30/72* (2013.01); *G01N 33/561* (2013.01); *G01N 2333/4716* (2013.01); *G01N 2400/00* (2013.01)

(58) Field of Classification Search
None
See application file for complete search history.

(56) References Cited

U.S. PATENT DOCUMENTS

| 2012/0040861 A1* | 2/2012 | Williams | ......... G01N 33/57438 |
| | | | 702/19 |
| 2012/0295288 A1 | 11/2012 | Yu et al. | |
| 2014/0038844 A1 | 2/2014 | Borrebaeck et al. | |

FOREIGN PATENT DOCUMENTS

| CN | 1726395 | 1/2006 |
| CN | 101438167 | 5/2009 |
| CN | 101680896 | 3/2010 |
| CN | 10353459 | 1/2014 |
| CN | 102137681 | 12/2014 |
| EP | 0274264 | 7/1988 |
| JP | 2007-051880 | 1/2007 |
| JP | 2014-020930 | 3/2014 |
| KR | 10-2013-0034505 | 4/2013 |
| KR | 10-2013-0116433 | 10/2013 |
| WO | WO-2004055519 A2 * | 7/2004 |
| WO | WO 2004/055519 | 3/2011 |
| WO | WO 2012/120288 | 9/2012 |

OTHER PUBLICATIONS

Tempero et al. Relationship of carbohydrate antigen 19-9 and lewis antigens in pancreatic cancer. Cancer Research 47: 5501-5503, Oct. 15, 1987.*
UniProtKB-P00751 (CFAB_HUMAN). pp. 1-14, Printed Aug. 7, 2018.*
Decision to Grant dated Jan. 28, 2016 From the Korean Intellectual Property Office Re. Application No. 10-2016-0004205 and Its Translation Into English. (3 Pages).
Decision to Refuse a Patent dated Nov. 26, 2015 From the Korean Intellectual Property Office Re. Application No. 10-2014-0056585 and Its Translation Into English. (4 Pages).
International Search Report and the Written Opinion dated Feb. 12, 2015 From the Korean Intellectual Property Office Re. Application No. PCT/KR2014/008242 and Its Translation of Search Report Into English. (17 pages).
Notification of Reason for Refusal dated May 28, 2015 From the Korean Intellectual Property Office Re. Application No. 10-2014-0056585 and Its Translation Into English. (5 Pages).
Lee et al. "Identification of Human Complement Factor B as a Novel Biomarker Candidate for Pancreatic Ductal Adenocarcinoma", Journal of Proteome Research, 13(11): 4878-4888, Jul. 24, 2014.
Pang et al. "Can the Acute-Phase Reactant Proteins Be Used as Cancer Biomarkers?", The International Journal of Biological Markers, 25(1): 1-11, Jan. 2010.
Schwaeble et al. "Complement Factor B [*Homo sapiens*]", Database NCBI [Online], GenBank Accession: AAD139891, Database Accession No. AAD13989, Jun. 5, 2000.
Communication Relating to Results of the Extended European Search Report dated Aug. 30, 2017 From the European Patent Office Re. Application No. 14892029.1. (7 pages).
Notice of Reasons for Rejection dated Sep. 26, 2017 From the Japanese Patent Office Re. Application No. 2016-567615 and its Translation into English.

(Continued)

*Primary Examiner* — Alana Harris Dent
(74) *Attorney, Agent, or Firm* — Sughrue Mion, PLLC

(57) ABSTRACT

The present application relates to a kit for diagnosing pancreatic cancer, a method for providing information for diagnosing pancreatic cancer using the kit, and a method for diagnosing pancreatic cancer using same, wherein the kit includes an antibody specifically binding to complement factor B protein and an antibody specifically binding to carbohydrate antigen 19-9 protein. According to the present application, it is possible to provide a marker for diagnosing pancreatic cancer having enhanced sensitivity and specificity.

11 Claims, 8 Drawing Sheets

Specification includes a Sequence Listing.

(56) References Cited

OTHER PUBLICATIONS

Office Action and Search Report dated Aug. 21, 2017 From the State Intellectual Property Office of the People's Republic of China Re. Application No. 201480078913.3 and its Translation into English. (17 pages).

Darvinche et al. "UniProtKB—P00751 (CFAB_HUMAN)", Apr. 16, 2014, 15 pages.

Poruk et al. "The Clinical Utility of CA 19-9 in Pancreatic Adenocarcinoma: Diagnostic and Prognostic Updates," Current Molecular Medicine, 13(3): 340-351, 2013.

Wingren et al. "Identification of Serum Biomarker Signatures Associated with Pancreatic Cancer," Cancer Research, 72(10): 2481-2490, May 15, 2012.

\* cited by examiner

SEQUENCE LISTING

```
<160> NUMBER OF SEQ ID NOS: 5

<210> SEQ ID NO 1
<211> LENGTH: 764
<212> TYPE: PRT
<213> ORGANISM: Homo sapiens
<220> FEATURE:
<221> NAME/KEY: human complement factor B
<222> LOCATION: (1)..(764)

<400> SEQUENCE: 1

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
                20                  25                  30

Pro Gln Gly Ser Cys Ser Leu Glu Gly Val Glu Ile Lys Gly Gly Ser
            35                  40                  45

Phe Arg Leu Leu Gln Glu Gly Gln Ala Leu Glu Tyr Val Cys Pro Ser
        50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
                100                 105                 110

Glu Tyr Trp Pro Arg Ser Pro Tyr Tyr Asn Val Ser Asp Glu Ile Ser
            115                 120                 125

Phe His Cys Tyr Asp Gly Tyr Thr Leu Arg Gly Ser Ala Asn Arg Thr
        130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190
```

-continued

Arg Gly Leu Thr Leu Arg Gly Ser Gln Arg Thr Cys Gln Glu Gly
        195                 200                 205

Gly Ser Trp Ser Gly Thr Glu Pro Ser Cys Gln Asp Ser Phe Met Tyr
210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
        275                 280                 285

Ala Lys Lys Cys Leu Val Asn Leu Ile Glu Lys Val Ala Ser Tyr Gly
        290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
        370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
        450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
        530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

```
Leu Pro Pro Thr Thr Thr Cys Gln Gln Gln Lys Glu Glu Leu Leu Pro
    610                 615                 620
Ala Gln Asp Ile Lys Ala Leu Phe Val Ser Glu Glu Lys Lys Leu
625                 630                 635                 640
Thr Arg Lys Glu Val Tyr Ile Lys Asn Gly Asp Lys Lys Gly Ser Cys
                    645                 650                 655
Glu Arg Asp Ala Gln Tyr Ala Pro Gly Tyr Asp Lys Val Lys Asp Ile
                660                 665                 670
Ser Glu Val Val Thr Pro Arg Phe Leu Cys Thr Gly Gly Val Ser Pro
                675                 680                 685
Tyr Ala Asp Pro Asn Thr Cys Arg Gly Asp Ser Gly Gly Pro Leu Ile
    690                 695                 700
Val His Lys Arg Ser Arg Phe Ile Gln Val Gly Val Ile Ser Trp Gly
705                 710                 715                 720
Val Val Asp Val Cys Lys Asn Gln Lys Arg Gln Lys Gln Val Pro Ala
                    725                 730                 735
His Ala Arg Asp Phe His Ile Asn Leu Phe Gln Val Leu Pro Trp Leu
                740                 745                 750
Lys Glu Lys Leu Gln Asp Glu Asp Leu Gly Phe Leu
    755                 760

<210> SEQ ID NO 2
<211> LENGTH: 21
<212> TYPE: DNA
<213> ORGANISM: Artificial
<220> FEATURE:
<223> OTHER INFORMATION: CFB forward primer

<400> SEQUENCE: 2
caacagaagc ggaagatcgt c                                           21

<210> SEQ ID NO 3
<211> LENGTH: 21
<212> TYPE: DNA
<213> ORGANISM: Artificial
<220> FEATURE:
<223> OTHER INFORMATION: CFB reverse primer

<400> SEQUENCE: 3
tatctccagg tcccgcttct c                                           21

<210> SEQ ID NO 4
<211> LENGTH: 20
<212> TYPE: DNA
<213> ORGANISM: Artificial
<220> FEATURE:
<223> OTHER INFORMATION: GAPDH forward primer

<400> SEQUENCE: 4
accacagtcc atgccatcac                                             20

<210> SEQ ID NO 5
<211> LENGTH: 20
<212> TYPE: DNA
<213> ORGANISM: Artificial
<220> FEATURE:
<223> OTHER INFORMATION: GAPDH reverse primer

<400> SEQUENCE: 5
tccaccaccc tgttgctgta                                             20
```

METHODS FOR DETECTING AN AMOUNT OF COMPLEMENT FACTOR B PROTEIN AND CARBOHYDRATE ANTIGEN 19-9 PROTEIN, AND METHODS FOR DIAGNOSING AND TREATING PANCREATIC CANCER USING THE SAME

RELATED APPLICATIONS

This application in a Continuation-in-Part (CIP) of PCT Patent Application No. PCT/KR2014/008242 having International filing date of Sep. 3, 2014, which claims the benefit of priority of Korean Patent Application No. 10-2014-0056585 filed on May 12, 2014. The contents of the above applications are all incorporated by reference as if fully set forth herein in their entirety.

SEQUENCE LISTING STATEMENT

The ASCII file, entitled 68137SequenceListing.txt, created on Nov. 8, 2016, comprising 7,221 bytes, submitted concurrently with the filing of this application is incorporated herein by reference.

FIELD AND BACKGROUND

The present application relates to a diagnostic kit for pancreatic cancer comprising an antibody specifically binding to a complement factor B protein and an antibody specifically binding to a carbohydrate antigen 19-9 protein, a method for providing information for diagnosing pancreatic cancer using the same and a method for diagnosing pancreatic cancer using the same.

Pancreatic cancer (PC; pancreatic ductal adenocarcinoma) caused 330 000 deaths globally in 2012 (WHO Cancer Report 2014) and is predicted to be one of the top three cancer killers along with lung and liver cancers in 2030 (Rahib, L et al., Cancer Res., 2014, 75, 2913-21). According to the 'Cancer Statistics 2013 Report', pancreatic cancer not only progresses rapidly but also readily metastasizes to lymph nodes; therefore, early symptoms are rarely recognized and the 5-year survival rate of patients diagnosed with PC is only 1 to 3% (Siegel, R et al., 2013, Ca. Cancer J. Clin. 63, 11-30) Although the surgical removal of tumors is a treatment option, early diagnosis remains difficult and challenging (Lee et al., 2014, J. Proteome Res., 13, 4878-).

One of the causes for lower 5-year survival rate after diagnosis of pancreatic cancer is mainly due to the lack of early diagnosis method or tool, which makes extremely difficult to treat the cancer patients at early stages of disease. Most of symptoms of pancreatic cancer do not appear until it significantly progresses, and thus once pancreatic cancer has been diagnosed, it has already metastasized, so that the surgery is often impossible. In addition, even if the surgery is possible, 80-90% of patients with surgical operation suffers a relapse and lead to death. In order to treat pancreatic cancer patients who received a curative surgery, radiation and chemotherapy are usually implemented but most cases show a limited effect on the survival time of the patient. Therefore, it is very important to diagnose pancreatic cancer at an early stage.

For diagnosis of pancreatic cancer, currently there are several imaging tests of pancreas, which include CT scan for making detailed cross-sectional images of your body, MRI scans for creating detailed images of parts of body and Ultrasound tests for making images of the pancreas (source: American Cancer Society website).

In addition, there are also the blood-based diagnoses which measure particular overexpressed protein in the pancreatic cancer patients' body fluids, such as blood plasma. Currently the most common tumor marker associated with pancreatic cancer is carbohydrate antigen 19-9 (CA 19-9). However, CA 19-9 is elevated in the blood plasma of those patients with cancers of the digestive systems including the biliary tract besides pancreatic cancer, and also in cases of cholangitis without malignant tumor and biliary obstruction, and thus it has very low specificity and sensitivity). In addition, it cannot be used in the early diagnosis, because the normal blood levels of CA 19-9 marker in early cancer appear in many diseases. For example, CA 19-9 is expressed in benign diseases and many types of gastrointestinal cancer (Rosty, C. et al., 2002; Engelen M J et al., 2000; Wu C S et al., 2012).

Meanwhile, complement factor B (CFB), which is one of the key ingredients in alternative pathways of complement activation, has been emerged as a potential diagnostic serologic marker for pancreatic cancer (Lee M J et al., 2014). Alternative pathways are activated by sugar structures on cell surfaces of pathogens, regardless of formation of the antigen-antibody complex. First, the activation is induced by combining a small amount of C3b present in the blood to surfaces of microorganisms. When the C3b is combined with complement factor B in the blood, it is degraded by complement factor D into C3bBb and Ba, in which the C3bBb is stabilized by properidine to generate C3 convertase of the alternative pathway and to enter the amplification phase that create more C3b. As a result, more C3 convertase is generated, and the resulting C3 convertase and C3b are combined to the cell surfaces of microorganisms to form C3bBb3b complex. The formed C3bBb3b complex represents C5 convertase action of the alternative pathway, and degrades C5 into C5a and C5b and finally forms MAC on bacterial surfaces. As a result, the bacteria die, and the antigen is eliminated. Complement factor B is known as a secreted protein playing an important role in generating C5 by combining C3b protein in the initial phase of this alternative pathway, and contains 5 N-glycosylation sites as glycoprotein.

Complement factor B is known to be secreted in sera of various patients suffering from ovarian cancer (Wu. J., et al., JPR, 4541-52, 2012), epipharynx cancer (Seriramalu. R., et al., Electrophoresis, 2388-95, 2010), breast cancer (Doustjalali, S R, et al., Electrophoresis, such as, 2392-401, 2004). Recently, it was shown that IL-6, produced by Pancreatic Stellate Cells—Conditioned Medium highly induced upregulation of CFB, suggesting its association with the progression of pancreatic cancer (Hamada, S. et al., 2016).

However, there was no attempt to diagnose pancreatic cancer with a combination of complement factor B and CA 19-9.

SUMMARY OF THE INVENTION

Accordingly, the present application is intended to provide a kit for diagnosing pancreatic cancer comprising an antibody specifically binding to a complement factor B protein, which is a novel biomarker for diagnosing pancreatic cancer having excellent specificity and sensitivity, and an antibody specifically binding to a carbohydrate antigen 19-9 protein, a method for detecting an amount of biomarker using the same, a method of screening for pancreatic cancer using the same and a method for diagnosing pancreatic cancer using the same. Especially, the present invention is characterized by providing a screening method, a detecting method or a diagnosing method which can see in the early stage whether or not pancreatic cancer is present using the biomarker.

The present application provides a method for detecting an amount of biomarker, a method for diagnosing pancreatic cancer, and a method of screening for pancreatic cancer, which comprise measuring the protein amount of complement factor B in the blood sample separated from a subject.

The present application provides a use as a diagnostic marker for pancreatic cancer of complement factor B (CFB) or/and carbohydrate antigen 19-9 (CA 19-9). More specifically, the present application provides a kit for diagnosing pancreatic cancer comprising an antibody specifically binding to complement factor B protein and carbohydrate antigen 19-9, respectively.

In one embodiment, the complement factor B protein may be one consisting of the amino acid sequence of SEQ ID NO. 1.

```
SEQ ID NO. 1:
MGSNLSPQLCLMPFILGLLSGGVTTTPWSLARPQGSCSLEGVEIKGGSFR

LLQEGQALEYVCPSGFYPYPVQTRTCRSTGSWSTLKTQDQKTVRKAECRA

IHCPRPHDFENGEYWPRSPYYNVSDEISFHCYDGYTLRGSANRTCQVNGR

WSGQTAICDNGAGYCSNPGIPIGTRKVGSQYRLEDSVTYHCSRGLTLRGS

QRRTCQEGGSWSGTEPSCQDSFMYDTPQEVAEAFLSSLTETIEGVDAEDG

HGPGEQQKRKIVLDPSGSMNIYLVLDGSDSIGASNFTGAKKCLVNLIEKV

ASYGVKPRYGLVTYATYPKIWVKVSEADSSNADWVTKQLNEINYEDHKLK

SGTNTKKALQAVYSMMSWPDDVPPEGWNRTRHVIILMTDGLHNMGGDPIT

VIDEIRDLLYIGKDRKNPREDYLDVYVFGVGPLVNQVNINALASKKDNEQ

HVFKVKDMENLEDVFYQMIDESQSLSLCGMVWEHRKGTDYHKQPWQAKIS

VIRPSKGHESCMGAVVSEYFVLTAAHCFTVDDKEHSIKVSVGGEKRDLEI

EVVLFHPNYNINGKKEAGIPEFYDYDVALIKLKNKLKYGQTIRPICLPCT

EGTTRALRLPPTTTCQQQKEELLPAQDIKALFVSEEEKKLTRKEVYIKNG

DKKGSCERDAQYAPGYDKVKDISEVVTPRFLCTGGVSPYADPNTCRGDSG

GPLIVHKRSRFIQVGVISWGVVDVCKNQKRQKQVPAHARDFHINLFQVLP

WLKEKLQDEDLGFL
```

In one embodiment, the subject may be a patient suspected of having pancreatic cancer.

In the present specification, the term "an amount of" can be replaced by "an expression level of" or "a concentration of".

In one embodiment, the method according to the present invention may further comprise a step of comparing the protein expression level of complement factor B in the blood sample separated from an subject to the complement factor B protein expression level of reference.

In the present specification, the term "reference" refers to a blood sample separated from a healthy subject without pancreatic cancer or/and other diseases, and the term can be replaced by "normal control group", "subject not having pancreatic cancer" or "healthy group".

In one embodiment, if on comparing the two samples the protein expression levels of complement factor B in the sample of the patient suspected of having pancreatic cancer is higher than the protein expression level of complement factor B in the sample of the normal control group, the above candidate patient can be classified as a patient with pancreatic cancer. For example, if the protein level of complement factor B in the sample of the candidate patient with pancreatic cancer is twice or more higher than the protein level of complement factor B in the sample of the normal control group, the above candidate patient can be classified as the patient with pancreatic cancer.

In one embodiment, if the concentration (or amount) of complement factor B in the sample of a subject is more than 78.4 ng/ml, the subject can be classified as a patient with pancreatic cancer. Specifically, the concentration of complement factor B may be measured by ELISA.

In one embodiment, the blood sample may be whole blood, plasma or a serum sample.

In the present application the term "diagnosis" means to determine the presence or characteristics of the pathology. In view of the purpose of this application, the diagnosis is to determine whether the generation and recurrence of pancreatic cancer is.

In the present application the term "screening" means selecting a subject to be expected to have a specific disease among a plurality of subjects or selecting a sample containing over certain amount of the target material among a plurality of samples. In view of the object of the present invention, the "screening" means selecting a subject that pancreatic cancer is created and/or relapsed among a plurality of subjects or selecting a sample comprising over certain amount of the biomarkers among a plurality of samples obtained from the subjects.

In the present application the term "detecting" means confirming the presence of any target material or the amount of the present material. In view of the object of the present invention, the "detecting" means confirming the presence of the biomarkers in a sample or the amount of the biomarkers present in the sample.

In the present application the term "biomarker", "marker for diagnosis" or "diagnostic marker" is a substance that can allow diagnosing or determining the presence of cancer cells by distinguishing cancer cells from normal cells. The marker which includes organic biomolecules, such as polypeptides or nucleic acids (for example: mRNA, etc.), lipids, glycolipids, glycoproteins or sugars (monosaccharides, disaccharides, oligosaccharides, etc.), increased or decreased in cancer cells over the normal cells. In view of the purposes of this application, pancreatic cancer diagnostic markers are genes of CA 19-9 and/or complement B and proteins encoding by them to show specifically high level of expression in pancreatic cancer cells over normal pancreatic tissue cells.

In the present application the term "measuring a protein expression level" is a procedure to determine the presence of the expressed proteins by cancer marker genes and amount of the expressed proteins in the biological sample, in which the amount of the protein is confirmed using the antibody to bind specifically to the proteins of the above genes. The analysis method for this includes, but is not limited to, western blotting, ELISA (enzyme linked immunosorbent assay), radioimmunoassay (RIA), radio immune diffusion, Ouchterlony immune diffusion, rocket immune electrophoresis, tissue immune staining, immune precipitation assay, complement fixation assay, FACS and protein chip, and the like.

By "specifically binding" in the present invention, it means that the bonding force to a targeted substance is excellent enough to be capable of detecting the presence of the targeted substance by bond over other substances.

In the present application "antibody" stands for the substantially encrypted peptide or polypeptide derived from an immunoglobulin gene or immunoglobulin genes, or the fragments thereof or made patterned after them, being capable of specifically binding to the antigen or epitope. In the present application the antibody includes a whole antibody and antibody fragments and includes various types of antibody structures without limiting thereto. The antibody fragment comprises parts of the full length antibody, variable domains of the antibody, or at least antigen biding sites of the antibody. Examples of antibody fragments include a diabody, a single-chain antibody molecule and a multi-specific antibody formed from the antibody fragments.

In one embodiment, the antibody may be a polyclonal antibody or a monoclonal antibody. Antibodies to complement factor B protein may be prepared by methods being usually carried out in the art, for example, fusion methods (Kohler and Milstein, European Journal of Immunology, 6: 511-519 (1976)), recombinant DNA methods (U.S. Pat. No. 4,816,56) or phage antibody library methods (Clackson et al, Nature, 352:624-628 (1991) and Marks et al, J. Mol. Biol., 222:58, 1-597 (1991)). General procedures for preparation of the antibody are described in detail in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, NY, 1991. For example, hybridoma cells to produce monoclonal antibodies are prepared by fusion of immortal cell lines to the antibody-producing lymphocytes, and the art required for this procedure is well known to one of ordinary skill in the art, which can be easily implemented. Polyclonal antibodies can be obtained by injecting the complement factor B protein antigen to the appropriate animal and collecting antisera from this animal, and then, separating the antibodies from the antisera using the known affinity technique.

In the present application the term, "sensitivity" represents the probability that the diagnostic test result will be positive with having suffered from the corresponding disease, whereas "specificity" represents the degree of possibility that the test result will be negative without having suffered from any disease.

Complement factor B proteins were selected as candidate substances for pancreatic cancer diagnostic marker to confirm the presence of the complement factor B protein from the plasmas of normal person and pancreatic cancer patients, and observe the change. As a result, it was confirmed that the protein expression level of complement factor B in the plasma of the pancreatic cancer patients was very high compared with the normal control group (Examples 1 and 2). In addition, when compared with CA 19-9 known as the existing pancreatic cancer diagnostic marker, the ELISA and ROC (Receiver Operating Characteristic) curve analysis were performed to verify the efficacy as a diagnostic marker for pancreatic cancer of the CFB, and sensitivity and specificity of CFB and CA 19-9 each were analyzed based on their optimal cut-off values (Examples 3 to 6). As a result, it could be seen that the expression of CA 19-9 also increases in liver cancer, bile duct cancer and stomach cancer, including pancreatic cancer, and thus the specificity is lowered. That is, it means that the CA 19-9 alone is not suitable to use as a diagnostic marker of pancreatic cancer. However, since the expression of the CFB was increased in only pancreatic cancer and it has excellent sensitivity and specificity, it means that the CFB is suitable as a marker for diagnosing pancreatic cancer.

In addition, in one embodiment of the present invention, it was confirmed whether the pancreatic cancer patient in the early state may be distinguished and diagnosed using the CFB. As a result, it was confirmed that the CFB could very well distinguish the pancreatic cancer patient in the early stage (Stage I, II) from normal persons, chronic pancreatitis patients and pancreatic cancer patents in the later phase (Stage III, IV), and thus it was confirmed that the CFB could be suited to the diagnostic marker of the early pancreatic cancer.

In this aspect, the biomarkers of the present invention may be diagnostic markers for the early pancreatic cancer, and the step of detecting an amount of the biomarker of the present invention, a method of screening a subject suffering from pancreatic cancer or a method for diagnosing pancreatic cancer may be detecting, screening and diagnosing the early pancreatic cancer or the subject suffering from pancreatic cancer.

Meanwhile, there is a problem that the CA 19-9 alone has lowered specificity as the pancreatic cancer diagnostic marker, but when used the CA 19-9 with the CFB, it could be seen to represent the most excellent sensitivity and specificity. This means that if the CA 19-9 alone, it is not suitable to use as a marker for diagnosing pancreatic cancer, whereas if the CA 19-9 is used together with the CFB, it can diagnose pancreatic cancer more accurately. In particular, according the present invention, when the CFB and the CA 19-9 are used together as biomarkers for diagnosing pancreatic cancer, it is possible to more accurately diagnose pancreatic cancer in the early stage.

Thus, in one embodiment, the kit may further comprise an antibody specifically binding to carbohydrate antigen 19-9.

The present application also provides a method for detecting an amount of biomarker, a method for diagnosing pancreatic cancer, and a method of screening for pancreatic cancer, which comprise measuring the protein expression levels of complement factor B and carbohydrate antigen 19-9 in the blood sample separated from a subject.

In one embodiment, the subject may be a patient group suspected of having pancreatic cancer.

In one embodiment, it may further comprise a step of comparing the protein expression levels of complement factor B and CA 19-9 in the blood samples isolated from a subject suspected of having pancreatic cancer with the protein expression levels of complement factor B and CA 19-9 in the normal control group. If on comparing the two samples all the protein expression levels of complement factor B and CA 19-9 in the sample of the subject suspected of having pancreatic cancer is higher than the protein expression levels of complement factor B and CA 19-9 in the sample of the normal control group, the above subject can be classified as a patient with pancreatic cancer. For example, if the protein level of complement factor B in the sample from a subject is twice or more higher than the protein level of complement factor B in the sample from the normal control group and the level of CA 19-9 in the sample from the subject is 37 U/ml or more, the above subject can be classified as the patient with pancreatic cancer. Furthermore, if the amount of CFB protein in the sample of a subject is more than 78.4 ng/ml, the above subject can be classified as the patient with pancreatic cancer. Wherein the amount of CFB protein may be measured by ELISA.

In one embodiment, the blood sample may be whole blood, plasma or a serum sample.

In a method for diagnosing pancreatic cancer comprising measuring the protein expression levels of complement factor B and carbohydrate antigen 19-9 as a biomarker for diagnosing pancreatic cancer, the present application also provides a method for diagnosing pancreatic cancer comprising the following steps:

a first step of collecting a blood sample from a subject;

a second step of contacting a portion of the blood sample with an antibody having specific binding affinity for complement factor B (CFB) and a detectable label, thereby forming a complex between the antibody and CFB;

a third step of contacting a portion of the blood sample with an antibody having specific binding affinity for carbohydrate antigen 19-9 (CA 19-9) and a detectable label, thereby forming a complex between the antibody and CA 19-9;

a fourth step of separating the complex formed in said contacting step (b) and (c) from labeled antibody not comprising the complex, respectively;

a fifth step of quantifying a signal from the detectable label of the antibody comprising the complex formed in said contacting step (b) and (c) respectively, the signal being proportional to an amount of CFB and CA19-9 in the blood sample, whereby the amount of CFB and CA19-9 in the sample is calculated, respectively;

a sixth step of comparing the amount of CFB and CA19-9 calculated in said quantifying step (e) to a reference amount of CFB and CA 19-9, respectively; and a seventh step of providing a diagnosis of pancreatic cancer in the subject if both the amount of CFB and CA 19-9 in the sample calculated in said quantifying step (e) are greater than each reference amount.

Here, the complement factor B and/or carbohydrate 19-9 refers to the biomarker for diagnosis of pancreatic cancer.

In the comparing step, since the signal from the detectable label of the biomarker-antibody complex is proportional to the amount of the biomarker in the blood sample, the amount of the biomarker can be seen from this.

In one embodiment, the amount of the biomarker in the control group refers to the amount of the biomarker in the blood sample of the subject without pancreatic cancer.

In one embodiment, the method for diagnosing pancreatic cancer in a subject is a method for diagnosing early stage pancreatic cancer (phase I or II) in a subject.

In one embodiment, the blood sample may be whole blood, plasma or a serum sample.

In one embodiment, it may further comprise a step of separating the CFB and/or CA19-9 from other proteins in the blood sample by immune precipitation between the collecting step and the step of contacting biomarkers with antibodies.

In one embodiment, the step of separating CFB and/or CA19-9 from other proteins may comprise the following steps:

i) a step of contacting the blood sample separated from the subject with the antibody specifically binding to the biomarker to form a complex between the antibody and the biomarker;

ii) a step of precipitating the complex formed in the step i);

iii) a step of separating the precipitated complex from the supernatant of the sample containing other proteins besides the biomarker and the antibody that does not form the complex.

The present invention also provides a method of screening a subject with pancreatic cancer. In the method for screening a subject with pancreatic cancer comprising measuring the protein expression levels of complement factor B and carbohydrate antigen 19-9 as a biomarker for diagnosing pancreatic cancer. The screening method comprising the following steps:

obtaining a human blood sample, and detecting the amount of complement factor B (CFB) protein and carbohydrate antigen 19-9 (CA 19-9) in the human blood sample respectively, wherein the CFB protein is detected by using an anti-CFB antibody;

wherein CA 19-9 is detected by using an anti-CA 19-9 antibody; and wherein the both amount of CFB and CA 19-9 are increased in comparison to amount of CFB and CA 19-9 in the sample of a subject not having pancreatic cancer.

wherein the amount of CFB protein is increased more than 2 fold in the sample of subject having pancreatic cancer in comparison to the sample of the subject not having pancreatic cancer;

wherein the amount of CFB protein is more than 78.4 ng/ml in the sample of subject having pancreatic cancer; and wherein the amount of CA 19-9 in the sample of subject having pancreatic cancer is more than 37 U/ml.

In one embodiment, the screening method is a method for screening a subject having early stage pancreatic cancer (phase I or II).

In one embodiment, if the protein level of complement factor B in a sample is twice or more higher than the protein level of complement factor B in the sample of the normal control group and the level of CA 19-9 in the sample is 37 U/ml or more, the above sample can be classified as being obtained from a subject suspected to having pancreatic cancer. Furthermore, if the amount of CFB protein in the sample is more than 78.4 ng/ml, the above sample can be classified as being obtained from a subject suspected to having pancreatic cancer. Wherein the amount of CFB protein may be measured by ELISA.

The present invention also provides a method for treating pancreatic cancer. The method comprises treating a subject, who is diagnosed with pancreatic cancer according to the above method, with therapeutic agent for pancreatic cancer. The therapeutic agent for pancreatic cancer may employ, without limitation, the known drugs with an effect of treating pancreatic cancer.

According to the present application the diagnostic marker of pancreatic cancer with improved sensitivity and specificity may be provided. In particular, the diagnostic markers of pancreatic cancer of the present invention may also diagnose the pancreatic cancer patient in the early stage with a high accuracy.

BRIEF DESCRIPTION OF THE SEVERAL VIEWS OF THE DRAWINGS

FIG. 1A shows a two-dimensional electrophoresis image of the plasma of a normal person, and FIG. 1B shows a two-dimensional electrophoresis image of the plasma of a pancreatic cancer patient. The spots indicated by the arrows refer to the complement factor B proteins.

DESCRIPTION OF SPECIFIC EMBODIMENTS OF THE INVENTION

Hereinafter, the present application is explained in detail through examples. The following examples are intended merely to illustrate the present application, to which the scope of the present application is not restricted.

[Example 1] Analysis of Protein Expression Levels of Complement Factor B (CFB)

Example 1-1. Detection of CFB Protein in Plasma by Gel Electrophoresis and Mass Spectrometry To detect the presence and amount of CFB in plasma of normal person and pancreatic cancer patients, electrophoresis and mass spectrometry were performed.

Plasmas were obtained from Gene Bank and Department of Gastroenterology in Severance Hospital according to regulations of the Institutional Review Board (IRB). Plasma samples were used by dispensing them by 200 µl and keeping them before the experiment at −70° C. Because complement factor B is a secreted protein and the known high abundance proteins are present in plasmas, proteins besides complement factor B were removed with Hu-14 (Agilent), and then two-dimensional electrophoresis was performed. For two-dimensional electrophoresis, 50 µg of each analytical sample and the reference sample corresponding thereto were labeled with 400 pmol of Cy3, Cy5, Cy2 (GE Healthcare) as a fluorescent dye under a dark condition for 30 minutes, and the reaction was stopped with 1 µL of 10 mM lysine. To be 450 µL finally by mixing three samples, each labeled with the fluorescent dye, with each other, the sample butter solution [6 M urea, 2 M thiourea, 4% Chaps, 60 mM dithiothreitol (DTT), 30 mM Tris, pH 8.5] was added, and rehydrated together with 2% IPG 4-7NL buffer solution at room temperature for 16 hours. Isoelectric focusing (IEF) was performed using Immobiline DryStrip pH 4-7NL (GE Healthcare) in MultiPhor II electrophoresis system (GE Healthcare) up to 95,000 V as the optimal requirement, and one-step reduction and alkylation were carried out with a tributylphosphine buffer solution [6 M urea, 2% sodium dodecyl sulfate (SDS), 30 mM Tris, 20% glycerol, 2.5% acrylamide solution, 5 mM tributylphosphine] for 25 minutes.

Figure 1A:
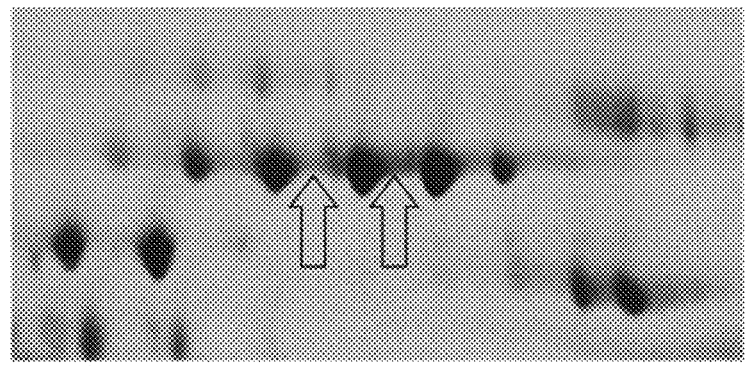
FIGS. 1A and 1B represents the electrophoresis image of the plasma.
Figure 1B:
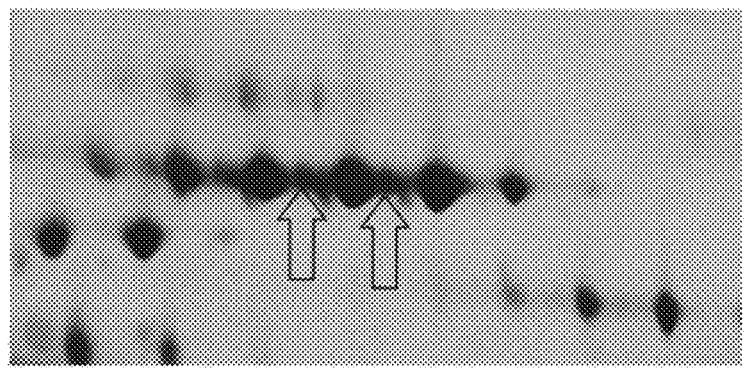

The two-dimensional electrophoresis results for plasmas of normal person were depicted in FIG. 1A, and the two-dimensional electrophoresis results for plasmas of pancreatic cancer patients were depicted in FIG. 1B. Arrows in the Figures indicate CFB. As a result, it could be seen that the expression of CFB increases.

Furthermore, in the plasmas of normal person and pancreatic cancer patients, the secondary vertical electrophoresis was performed to investigate the difference in expression of CFB. It was separated by using Ettan Dalttwelve electrophoresis system (GE Healthcare) for the secondary vertical electrophoresis and using 9%~16% polyacrylamide gel, and scanned by means of Typhoon 9400 (GE Healthcare) scanner with wavelengths corresponding to Cy2, Cy3, Cy5, after completing the electrophoresis. Each gel image was analyzed using DeCyder2-D analysis software (GE Healthcare).

Figure 2:
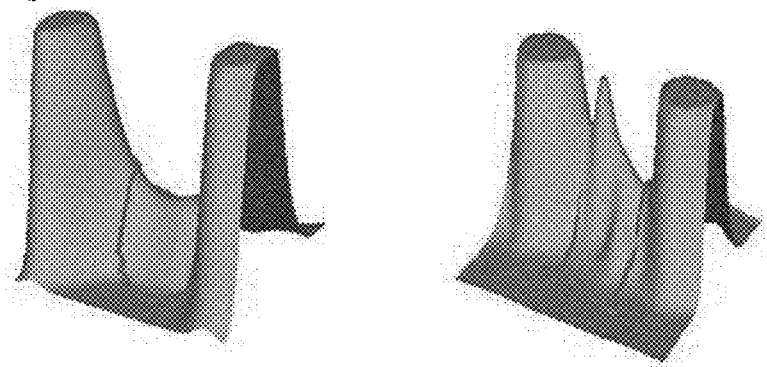
FIG. 2 represents the expression difference of the complement factor B in the plasma of the normal person and the plasma of the pancreatic cancer patient, which shows two-dimensional vertical electrophoresis images of the spot (black point) parts in FIGS. 1A and 1B.

As a result, just like the two-dimensional electrophoresis results, it could be seen in pancreatic cancer patients that the expression of CFB increases (FIG. 2).

After analyzing images, the mass spectrometry was performed on the spots indicated by the arrows in FIGS. 1A and 1b to investigate the presence of the CFB. Protein spots were picked from the gel stained with Coomassie blue dye, decolored and digested with trypsin, and then the digested peptides were desalted using a mixture of Poros R2 and Oligo R3 resins. Protein identification was analyzed by Q-TOF (Agilent), and the obtained spectrum by the Q-TOF-MS was identified using MASCOT database.

As a result, it could be confirmed, as shown in Table 1 below, that the spots indicated by the arrows in FIGS. 1A and 1B are CFB.

TABLE 1

| Number | Protein Name | pI Value | Score | Queries Matched Ratio | Sequence Coverage |
|---|---|---|---|---|---|
| gi291922 | Complement Factor B | 6.55 | 171 | 25 | 1.5 | 11% |

Example 1-2. Analysis of CFB Protein Expression Levels in Plasmas

To analyze the CFB protein expression levels in plasmas of patients with pancreatic cancer, the immunoblot was performed. The Western blot was performed by using antibodies from the same protein amounts in plasmas of 10 normal person and plasmas of 10 patients with pancreatic cancer. After 10% SDS-PAGE analysis about 10 μg of the plasma protein, the gel was transferred into nitrocellulose (NC) membrane for the Western blot and then was blocked with TBS-T buffer solution containing 5% skimmed milk[20 mM Tris, 137 mM sodium chloride, 0.1% Tween-20, pH 7.6] for 1 hour. Anti-complement factor B antibody (CFB, Abcam) was primarily treated by diluting it in the TBS-T buffer solution containing 5% skimmed milk by 1:1000 times, and anti-mouse IgG-HRP (Santa Cruz) was secondarily treated by 1:10000 times. The final NC membrane reacted with ECL Plus Western blot reagent (GE Healthcare) for 1 minute, and analyzed by scanning a Typhoon 9400 scanner.

Figure 3A:
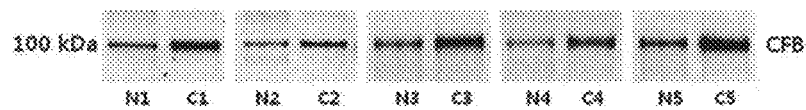
FIG. 3A shows the results of analyzing the protein expression levels of complement factor B in normal and pancreatic cancer patient plasmas by Western blot (N: normal, C: pancreatic cancer).

As a result, as depicted in FIG. 3A, it could be seen that the expression of CFB increases in the patient group with pancreatic cancer.

Figure 3B:
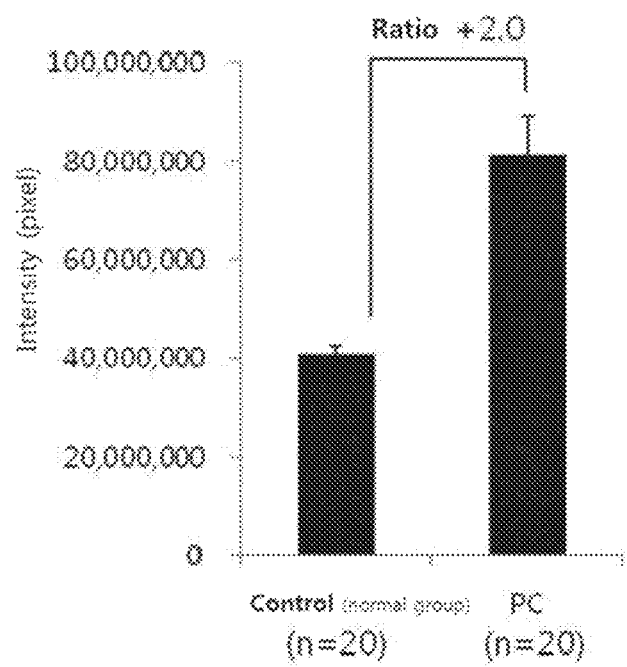
FIG. 3B is a graph showing the intensity of the Western blot band in FIG. 3A.

By analyzing the result of FIG. 3A through band intensity about fold ratios, it was confirmed that CFB is highly expressed in the plasmas of the patients with pancreatic cancer over the normal group (FIG. 3B).

Example 1-3. Analysis of CFB Expression Levels in Pancreatic Cancer Cells

Figure 4A:
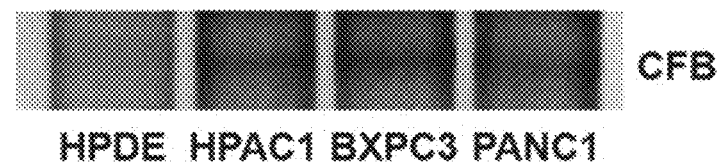
FIG. 4A shows the results of analyzing the protein expression levels of complement factor B in normal cell lines (HPDE) and pancreatic cancer cell lines (HPAC1, BXPC3, PANC1) by Western blot.

Western blotting and RT-PCR were performed to determine the CFB expression levels in the pancreatic cancer cell lines. HPDE (human pancreatic duct epithelial cell) was used as the normal cell lines, and HPAC1, BXPC3 (human pancreas adenocarcinoma epithelial cell), and PANC1 (human pancreas epithelioid carcinoma) were used as the pancreatic cell lines. 2 μg of anti-complement factor B antibody and 10 μl of protein G agarose were immune precipitated together in 1 ml tube for 2 hours, using 1 mg of each cell lysate, and then the CFB expression levels in the normal cells and the pancreatic cancer cells were determined via the Western blot. As a result, it was confirmed that CFB is not detected in the normal cells, but is detected only in pancreatic cancer cells (FIG. 4A).

Next, the mRNA expression level of CFB was determined by using RT-PCR. The total RNA was extracted using the easy-BLUE (iNtRON, Gyeonggi, Korea), and cDNA was synthesized using the omniscript RT kit (Qiagen, Hilden, Germany). The primers used were as follows:

```
CFB primer (SEQ ID NO. 2):
5'-CAACAGAAGCGGAAGATCGTC-3' (forward)

CFB primer (SEQ ID NO. 3):
5'-TATCTCCAGGTCCCGCTTCTC-3' (reverse)

GAPDH primer (SEQ ID NO. 4):
5'-ACCACAGTCCATGCCATCAC-3' (forward)

GAPDH primer (SEQ ID NO. 5):
5'-TCCACCACCCTGTTGCTGTA-3' (reverse)
```

Figure 4B:
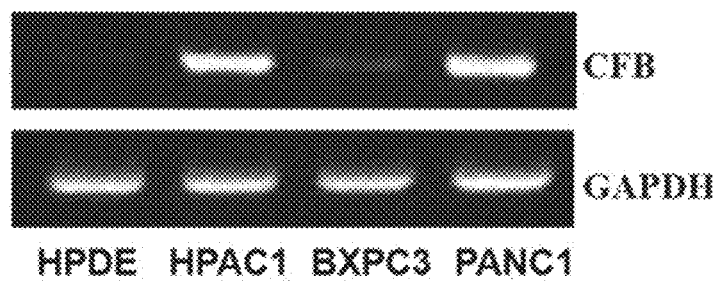
FIG. 4B shows the results of analyzing the protein expression levels of complement factor B in normal cell lines (HPDE) and pancreatic cancer cell lines (HPAC1, BXPC3, PANC1) by RT-PCR.
Figure 4C:
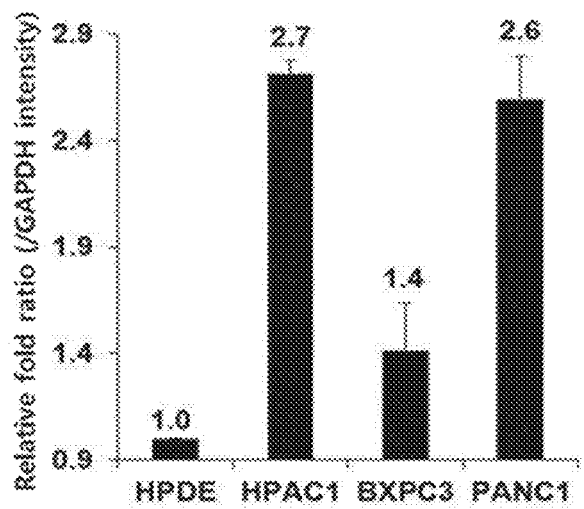
FIG. 4C is a graph showing the band intensity in FIG. 1B.

PCR conditions were 35 cycles, denaturation at 94° C. for 1 minute, annealing at 59° C. for 1 minute, and primer extension at 72° C. for 1 minute. As a result, it was confirmed as in the Western blot data that CFB is not detected in the normal cells, but is detected only in the pancreatic cancer cells (FIG. 4B). By analyzing the result of FIG. 1A through band intensity about fold ratios, it was confirmed that CFB is highly expressed in the pancreatic cancer cell lines over the normal cell lines (FIG. 4C).

[Example 2] Analysis of the Protein Expression Level of Complement Factor B (CFB) with a Plurality of Samples To ascertain a definite possibility as a biomarker candidate about CFB, the further independent confirmation experiment was performed using large patient cohorts.

The Western blot was performed in the same manner as Examples 1 to 3, using plasmas of 44 normal persons (HD), 12 pancreatitis patients (CP), and 40 pancreatic cancer patients (PC) and then using the pooled plasmas of the normal person as a standard.

Figure 5A:
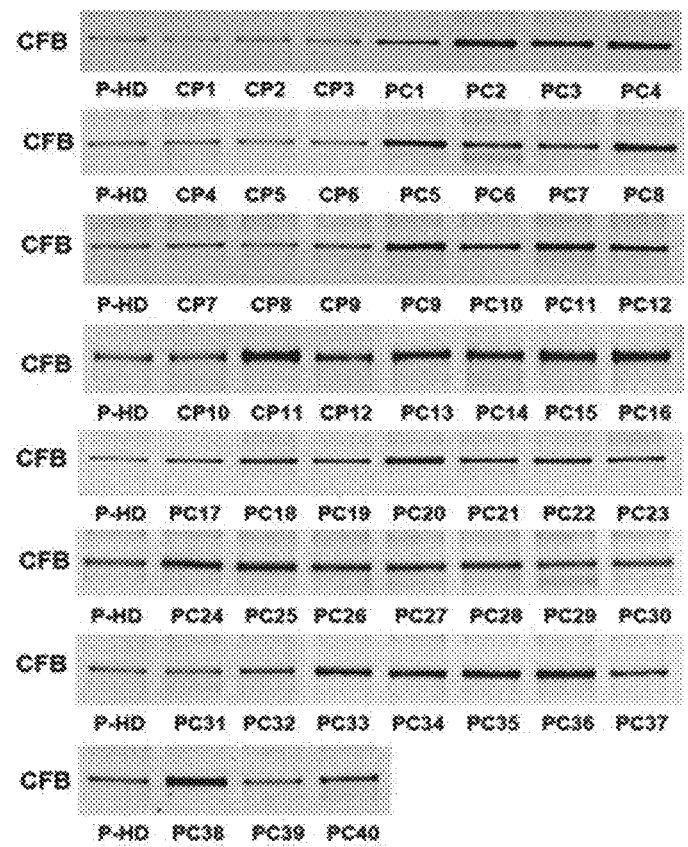
FIG. 5A is the results of analyzing the protein expression levels of complement factor B (CFB) by Western blot. HD represents normal, CP pancreatitis, and PC pancreatic cancer.
Figure 5B:
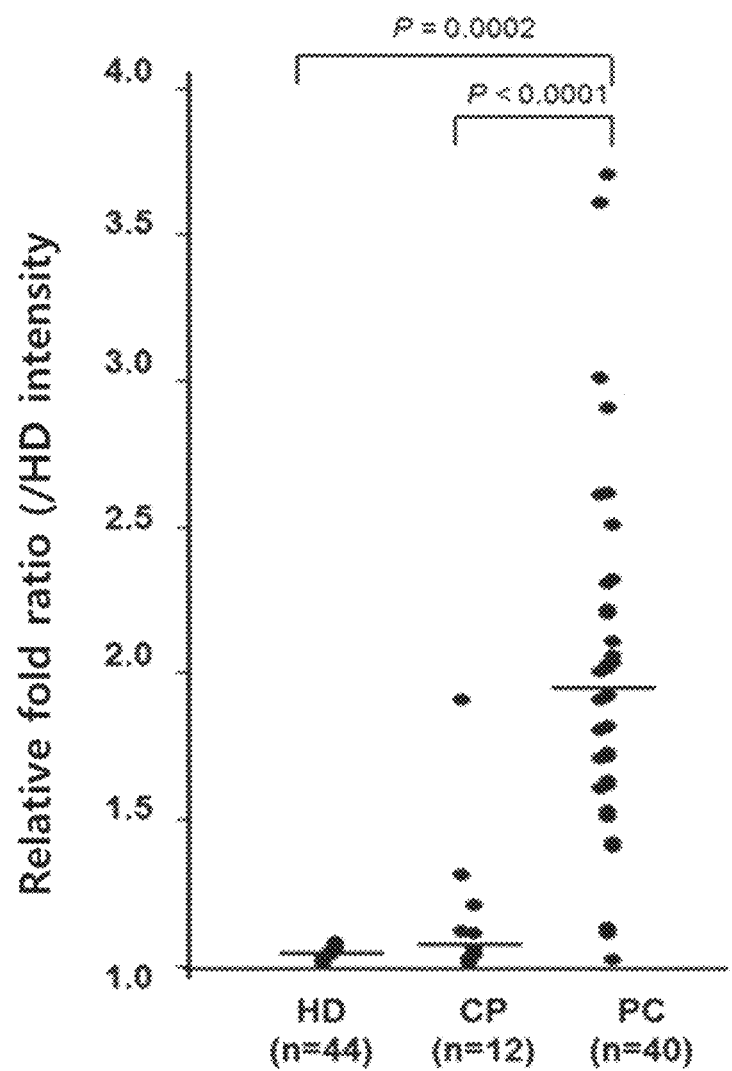
FIG. 5B is a graph showing the intensity of the Western blot band in FIG. 5a. HD represents normal, CP pancreatitis, PC pancreatic cancer.

As a result, it could be confirmed that CFB is highly expressed in PC over HD and CP (FIG. 5A), and it was demonstrated that CFB is highly expressed in PC over HD and CP, with being p<0.05 on indicating the intensity of the Western blot bands as points (FIG. 5B). Therefore, it could be confirmed that CFB is expressed twice as high as in PC over HD and CP, as significant values, even on performing the independent experiment using the large patient cohorts.

[Example 3] Analysis of Protein Expression Levels of CFB and CA 19-9 in Various Cancer Patients by ELISA To compare the expression levels of CA 19-9 and CFB, now known as pancreatic cancer biomarkers, ELISA tests were performed using plasmas of normal persons (HD), pancreatitis patients (CP), pancreatic cancer patients (PC), liver cancer patients (HCC), bile duct cancer patients (CC), and stomach cancer patients (GC). Products from USCN and Panomics were used as ELISA KITs of CFB and CA 19-9, respectively, and the experiments were carried out in accordance with each protocol for each product.

Figure 6A:
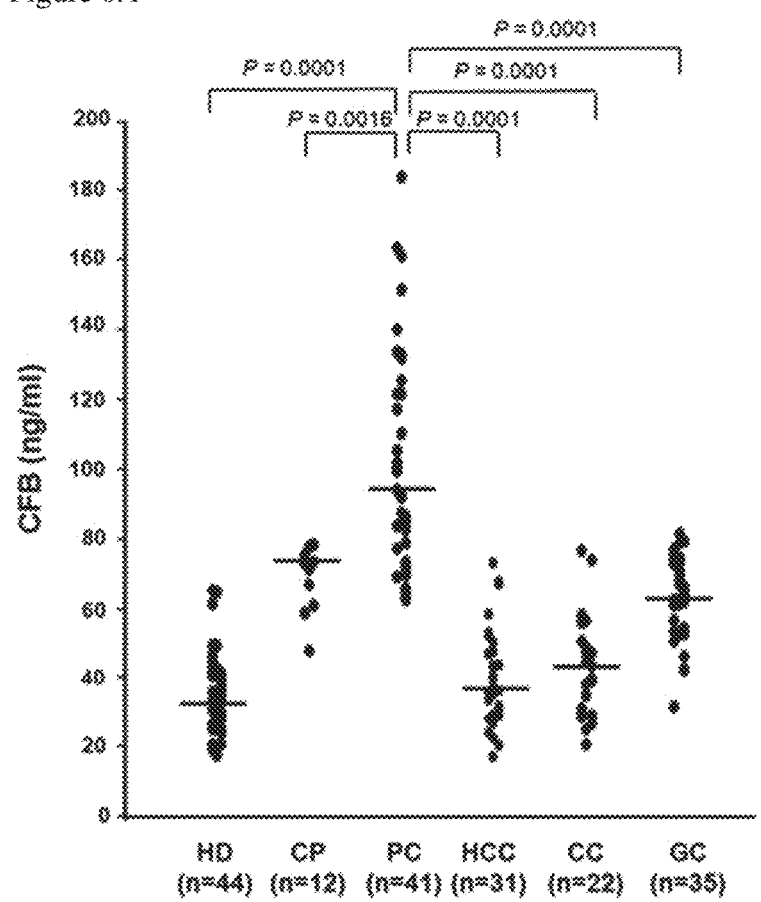
FIG. 6A shows the results of analyzing the expression levels of CFB in various cancers by the ELISA (a: CFB, b: CA 19-9). HD: normal persons group, CP: pancreatitis patients group, PC: pancreatic cancer patients group, HCC: liver cancer patients group, CC: bile duct cancer patients group and GC: stomach cancer patients group.

First, in the case of CFB ELISA, each plasma was diluted in 1:10,000, and then introduced by 100 μl into the wells overlaid with antibody to CFB. They were incubated for 2 hours at room temperature. Then, after removing plasmas from the wells and introducing 100 μl of a detection reagent a working solution therein, they were incubated for 1 hour at room temperature. After 1 hour, the solution was removed from the wells, and then they were washed three times repeatedly by adding 350 μl of the washing solution thereto. Then 100 μl of the detection reagent B working solution was introduced into each well and reacted at room temperature for 30 minutes. They were washed five times with the wash solution. Then 90 μl of the substrate solution was introduced into each well, and then reacted in the dark condition for 15 minutes, followed by quantification at 450 nm using a microplate reader after introducing 50 μl of the stop solution thereto. The expression levels of CFB in these groups appeared to be 34.0 (range: 26.1 to 41.3), 73.5 (range: 62.3 to 77.1), 92.0 (range: 75.2 to 121.6), 37.0 (range: 28.8 to 47.5), 41.5 (range: 29.1-52.1), 63.0 (range: 56.3 to 72.9) ng/ml (FIG. 6A).

Figure 6B:
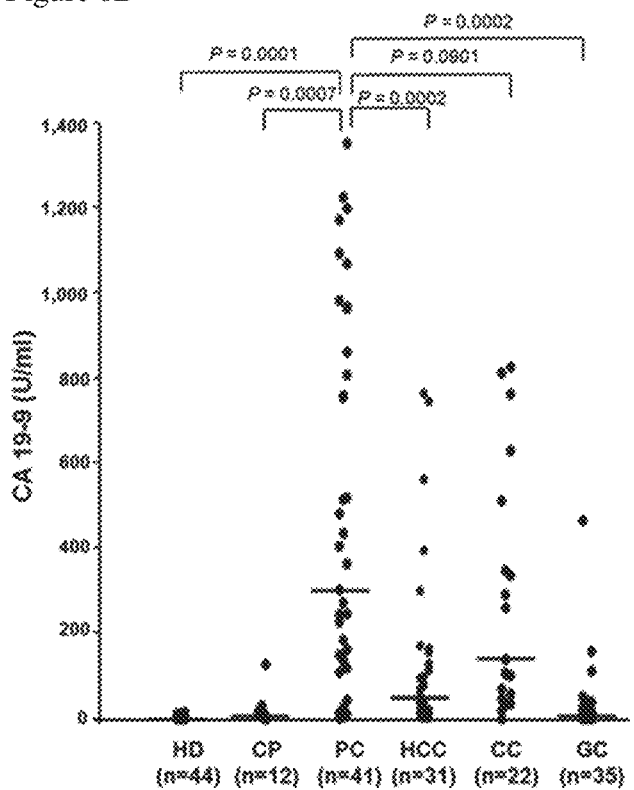
FIG. 6B shows the results of analyzing the expression levels of CA 19-9 in various cancers by the ELISA (a: CFB, b: CA 19-9). HD: normal persons group, CP: pancreatitis patients group, PC: pancreatic cancer patients group, HCC: liver cancer patients group, CC: bile duct cancer patients group and GC: stomach cancer patients group.

In the case of CA 19-9 ELISA, each of plasma was introduced by 10 μl into the plate overlaid with CFB19-9 antibody, and 100 μl of CA 19-9 assay buffer was introduced thereon. Then they were well mixed for 30 seconds, and then incubated at room temperature for 90 minutes. Then, the buffer was removed from the wells, which were washed four times repeatedly using the wash buffer. Then, 100 μl of the working conjugate reagent was carefully introduced into each well, and then incubated at room temperature for 90 minutes after well mixing them for 30 seconds. The reagent was removed from the wells, which were washed four times repeatedly using the wash buffer. Then, TMB was introduced into each well and reacted for 20 minutes in the dark conditions after mixing them for 10 seconds. Then, 100 μl of the stop solution was introduced thereto, and mixed for 30 seconds, followed by quantification at 450 nm using the microplate reader. The CA 19-9 levels in these groups each appeared to be 4.6 (range: 2.8 to 7.2), 10.2 (range: 6.0 to 21.4), 298.8 (range: 111.4 to 832.6), 50.5 (range: 18.1 to 159.5), 137.5 (range: 53.8 to 537.9), and 10.0 (range: 9.4 to 16.7) U/ml (FIG. 6B). The expression levels of CFB in the plasmas were particularly highly expressed as CA 19-9 in the PC group over non-PC group (HD, CP, HCC, CC, and GC) as CA 19-9 (p<0.002). Also, in the case of CFB, as compared with CA 19-9, it was demonstrated that it better distinguishes between the PC patents and non-PC patients (P<0.0001).

This means that CA 19-9 alone is not suitable for use as a diagnostic marker for pancreatic cancer, whereas CFB specifically increasing the expression in pancreatic cancer only is suitable as a marker for diagnosing pancreatic cancer.

Figure 7:
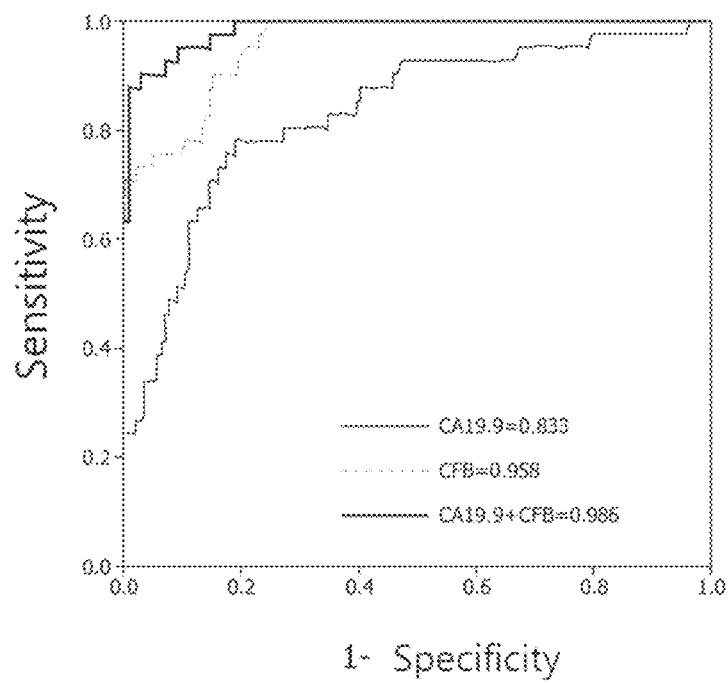
FIG. 7 shows ROC curves of CA 19-9, CFB and CFB+CA 19-9.

[Example 4] Analysis of Sensitivity and Specificity of CFB and CA 19-9 with ROC (Receiver Operating Characteristic) Curve, in Diagnosis of Pancreatic Cancer To determine how well CFB and CA 19-9 distinguish between the pancreatic cancer patients and person without pancreatic cancer (HD, CP, HCC, CC, and GC), the ROC curve analysis was performed using the Mann-Whitney rank sum test program. CFB was compared with CA 19-9 through the AUC value. As a result, the AUC value of CFB of 0.958 (95% CI: 0.956-0.959) appeared to be higher than the AUC value of CA 19-9 of 0.833 (95% CI: 0.829-0.837). The AUC value of 0.986 (0.985-0.986) on combining the two (CFB+ CA 19-9) showed a significantly higher AUC value than those (p<0.01) on using CFB and CA 19-9 alone (FIG. 7).

This means that it is possible to diagnose pancreatic cancer by CFB alone or a combination of CFB and CA 19-9.

[Example 5] Diagnosis of Pancreatic Cancer Based on Optical Cut-Off Values of CFB and CA 19-9

For each group (HD; normal, CP; pancreatitis, PC; pancreatic cancer, HCC; liver cancer, CC; bile duct cancer, GC; stomach cancer), the diagnostic efficiencies of CA 19-9 and CFB were confirmed. As a result, as shown in Table 2 below, both CA 19-9 and CFB showed the similar diagnostic efficiency in the PC (CA 19-9: 80.5%, CFB: 73.2%). However, CA 19-9 showed high diagnostic efficiency (HCC: 61.3%, CC: 77.2%, GC: 17.1%) for other cancers cancer (HCC, CC, GC), whereas CFB showed low diagnostic efficiency for other cancers (HCC: 0%, CC: 0%, GC: 8.6%). This means that CFB is more specific to PC than CA 19-9 as compared to other cancers.

TABLE 2

|    | CA 19-9 ≥ 37 U/ml | CFB ≥ 78.4 ng/ml |
|----|-------------------|------------------|
| HD | 0%                | 0%               |
| CP | 8.3%              | 8.3%             |

TABLE 2-continued

|     | CA 19-9 ≥ 37 U/ml | CFB ≥ 78.4 ng/ml |
|-----|-------------------|------------------|
| PC  | 80.5%             | 73.2%            |
| HCC | 61.3%             | 0%               |
| CC  | 77.2%             | 0%               |
| GC  | 17.1%             | 8.6%             |

[Example 6] Identification of Sensitivity and Specificity of CFB and CA 19-9

In order to assess the accuracy as a diagnostic indicator of pancreatic cancer of CFB, CA 19-9 and CFB+CA 19-9, sensitivity and specificity (%) of CA 19-9, CFB and CFB+ CA 19-9 in pancreatic cancer diagnosis compared with other diseases were identified according to the optical cut-off values predicted by the maximum Youden index. As a result, as shown in Table 3 below, when PC was compared with other groups (HD, CP, HCC, CC, and GC), the sensitivity of CA 19-9 appeared to be 80.4%, with being the specificity of 70.0%, and the sensitivity of CFB appeared to be 73.1%, with being the specificity of 97.9%. And when CFB and CA 19-9 were combined, the sensitivity appeared to be 90.1%, with being the specificity of 97.2%. This means that the better diagnostic efficiency on combining CA 19-9 and CFB appears over the cases of using CA 19-9 and CFB alone.

TABLE 3

|                       | CA 19-9 (U/ml)   | CFB (ng/ml)      | CA 19-9 + CFB    |
|-----------------------|------------------|------------------|------------------|
| PC vs. other cancers  | 37               | 78.42            | —                |
| Y-index               | 50.4             | 71.0             | 87.4             |
| Sensitivity (%; 95% CI) | 80.4 (79.8-81.0) | 73.1 (72.4-73.7) | 90.1 (89.7-90.6) |
| Specificity (%; 95% CI) | 70.0 (69.6-70.4) | 97.9 (97.8-98.1) | 97.2 (97.0-97.3) |

[Example 7] Analysis of Protein Expression Level of CFB and CA 19-9 in Pancreatic Cancer Progression Stage (Phase) Patients To compare the difference of expression levels of the CA 19-9 and the CFB in pancreatic cancer patients according to phase of pancreatic cancer progress, the expression levels of the CA 19-9 and the CFB were confirmed through ELISA using plasmas of 44 normal persons (HD), 12 chronic pancreatitis patents (CP), 50 pancreatic cancer (Stage I-II) patients, 39 pancreatic cancer (Stage III-IV) patients. The used CFB and CA 19-9 ELISA KITs were products from Abnova and Panomics, respectively, and the experiments were performed according to the protocol of each product.

First, in the case of the CFB ELISA, the plasmas were each diluted to 1:4,000, and then the diluted plasmas were each added by 50 μl to wells covered with an antibody to the CFB were laid. They were incubated at room temperature for 2 hours, and washed five times repeatedly by adding 200 μl of the washing solution thereto. The biotinylated antibody was added by 50 μl to each well and then incubated at room temperature for 1 hour. Then, they were washed five times repeatedly by adding 200 μl of the washing solution thereto. Each streptavidin-peroxidase was added by 50 μl to each well and then incubated at room temperature for 30 minutes. Then, they were washed five times repeatedly by adding 200 μl of the washing solution thereto. 50 μl of the substrate solution was added to each well and then reacted in a dark condition for 20 minutes, and after that, 50 µl of the stop solution was added and then quantified at 450 nm using a micro-plate reader.

In the case of the CA 19-9 ELISA, the plasmas were each added by 10 µl to well plates covered with the CA 19-9 antibody, on which 100 µl of the CA 19-9 assay buffer was put. Then, they were well mixed for 30 seconds and then incubated at room temperature for 90 minutes. Then, the buffer was removed from the wells, which were washed four times repeatedly using the wash buffer. Then, 100 µl of the working conjugate reagent was added to each well, well mixed for 30 seconds and then incubated at room temperature for 90 minutes. The reagent was removed from the wells, which were washed four times repeatedly using the wash buffer. Then, the TMB was added to each well, mixed for 10 seconds and reacted for 20 min in a dark condition. Then, 100 µl of the stop solution was added thereto, mixed for 30 seconds and quantified at 450 nm using a micro-plate reader.

Figure 8A:
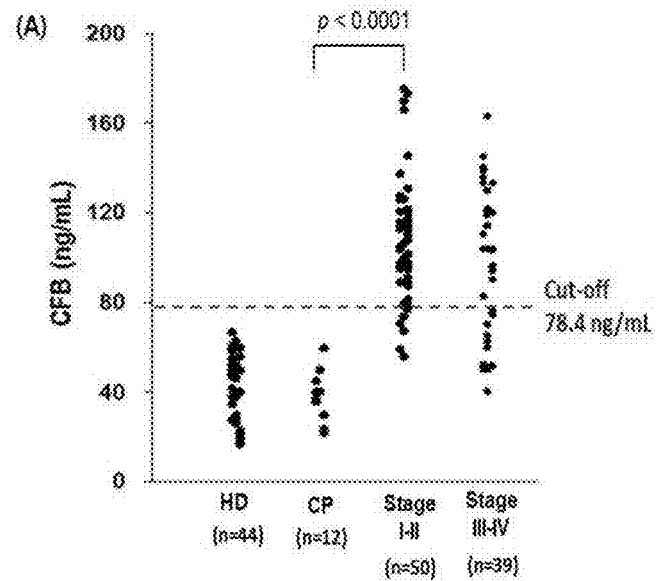
FIG. 8A is a graph identifying the expression degree of the CFB in normal persons, chronic pancreatitis patients, early pancreatic cancer patients (Stage I, II) and the terminal pancreatic cancer patients (Stage III, IV).
Figure 8B:
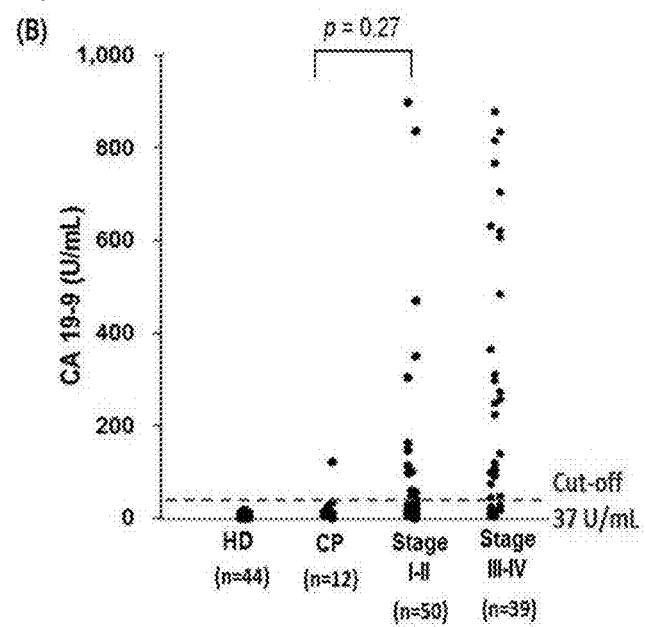
FIG. 8B is a graph identifying the expression degree of the CA 19-9 in normal persons, chronic pancreatitis patients, early pancreatic cancer patients (Stage I, II) and the terminal pancreatic cancer patients (Stage III, IV).

As shown in FIGS. 8A and 8B, it was confirmed that the case of CFB significantly distinguished the chronic pancreatitis group and the early stage patient (pancreatic cancer Stage I-II) group better than the CA 19-9. In addition, it was confirmed that while the CA 19-9 was much expressed in the Stage III-IV (the terminal stage) of pancreatic cancer, the CFB was much expressed in the Stage I-II of pancreatic cancer patients.

Figure 8C:
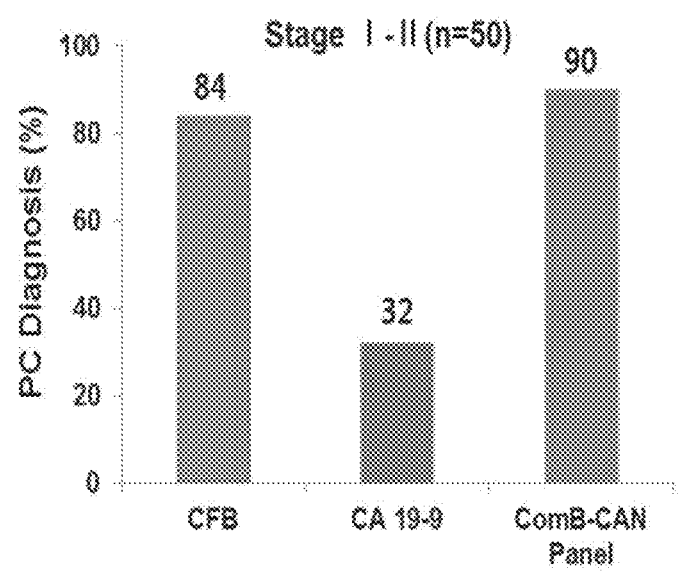
FIG. 8C is a graph identifying the Pancreatic Cancer diagnosis (%) by the expression degree of the CFB, CA 19-9 and a combination for CFB and CA 19-9 in early pancreatic cancer patients (Stage I, II).
Figure 8D:
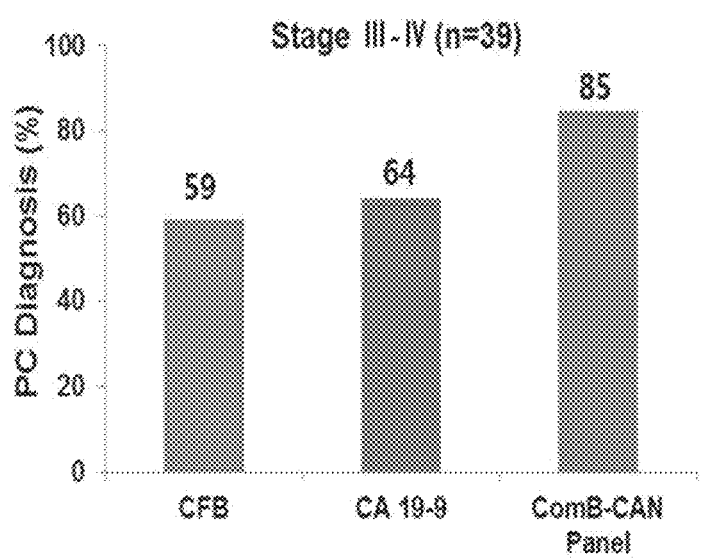
FIG. 8D is a graph identifying the Pancreatic Cancer diagnosis (%) by the expression degree of the CFB, CA 19-9 and a combination for CFB and CA 19-9 in the terminal pancreatic cancer patients (Stage III, IV).

In addition, on the basis of the above results, it was confirmed whether the CFB, the CA 19-9, and a combination of the CFB and the CA 19-9 could diagnose pancreatic cancer in the early stage of pancreatic cancer. As shown in FIGS. 8C and 8D, when the diagnostic rate of the CFB and the CA 19-9 for the pancreatic cancer patients was confirmed, the diagnostic rate of CFB in the early stage of pancreatic cancer appeared as 84%, whereas the CA 19-9 showed a low diagnostic rate of 32%. In particular, when the CFB and the CA 19-9 were combined (ComB-CAN Panel), it was confirmed that the early diagnostic rate increased up to 90%, which was a level higher than the diagnostic rate of the patients of pancreatic cancer Stage III/IV. Therefore, on the basis of the above results, it was confirmed that in the case of using the CFB of the present invention and the CA 19-9 together in diagnosing pancreatic cancer, the problem that the early diagnosis of pancreatic cancer was conventionally continued to be difficult could be overcome, it was also possible to distinguish it from pancreatitis, and pancreatic cancer could be early diagnosed with a high accuracy.

What is claimed is:

1. A method for diagnosing and treating pancreatic cancer in a subject, the method comprising the steps of:
   (a) collecting a blood sample from the subject;
   (b) detecting an amount of human complement factor B (CFB) protein and an amount of human carbohydrate antigen 19-9 (CA 19-9) in the blood sample of the subject respectively;
   (c) comparing the amount of CFB protein and the amount of CA19-9 detected in said step (b) to a reference amount of CFB protein and a reference amount of CA 19-9, respectively;
   (d) diagnosing the subject with pancreatic cancer and determining an absence of at least one disease or condition selected from the group consisting of pancreatitis, liver cancer, bile duct cancer, and stomach cancer when both the amount of CFB protein and the amount of CA 19-9 in the blood sample detected in said step (c) are greater than the respective reference amounts; and
   (e) treating the diagnosed subject by at least one of (i) administering an effective amount of a therapeutic agent for pancreatic cancer to the diagnosed subject, (ii) conducting a curative surgery, and (iii) conducting a radiation therapy,
   wherein the reference amounts are an amount of CFB protein and an amount of CA 19-9 in a blood sample from a subject not having pancreatic cancer, and
   wherein the CFB protein consists of the amino acid sequence of SEQ ID NO: 1.

2. The method according to claim 1, wherein the pancreatic cancer is phase I pancreatic cancer or phase II pancreatic cancer.

3. The method according to claim 1, wherein the blood sample is whole blood, blood plasma or serum sample.

4. The method of claim 1,
   wherein the subject is diagnosed with pancreatic cancer when the amount of CFB protein in the blood sample is more than 78.4 ng/ml.

5. A method of diagnosing and treating pancreatic cancer in a subject, the method comprising:
   obtaining a blood sample from the subject;
   detecting an amount of human complement factor B (CFB) protein and an amount of human carbohydrate antigen 19-9 (CA 19-9) in the blood sample of the subject respectively;
   diagnosing the subject with pancreatic cancer and determining an absence of at least one disease or condition selected from the group consisting of pancreatitis, liver cancer, bile duct cancer, and stomach cancer when both the amount of CFB protein and the amount of CA 19-9 in the blood sample are greater than an amount of CFB protein and an amount of CA 19-9 in a blood sample of a subject not having pancreatic cancer; and
   treating the diagnosed subject by at least one of (i) administering an effective amount of a therapeutic agent for pancreatic cancer to the diagnosed subject, (ii) conducting a curative surgery, and (iii) conducting a radiation therapy,
   wherein the CFB protein consists of the amino acid sequence of SEQ ID NO: 1.

6. The method of claim 5,
   wherein the subject is diagnosed with pancreatic cancer:
   when the amount of CFB protein in the blood sample is greater more than 2 fold than the amount of CFB protein in the blood sample of the subject not having pancreatic cancer; and
   when the amount of CA 19-9 in the blood sample is more than 37 U/ml.

7. The method of claim 5,
   wherein the subject is diagnosed with pancreatic cancer when the amount of CFB protein in the blood sample is more than 78.4 ng/ml.

8. The method of claim 5, wherein the pancreatic cancer is phase I pancreatic cancer or phase II pancreatic cancer.

9. The method of claim 5, wherein the blood sample is whole blood, serum or plasma sample.

10. The method of claim 1, wherein the amount of CFB protein and the amount of CA19-9 in the blood sample is detected using a two-dimensional fluorescence electrophoresis, Western blotting, ELISA, radioimmunoassay, radioimmunodiffusion, immune electrophoresis or mass spectrometry.

11. The method of claim 5, wherein the amount of CFB protein and the amount of CA19-9 in the blood sample is detected using a two-dimensional fluorescence electrophoresis, Western blotting, ELISA, radioimmunoassay, radioimmunodiffusion, immune electrophoresis or mass spectrometry.

* * * * *